United States Patent [19]
Duke

[11] Patent Number: 5,877,410
[45] Date of Patent: Mar. 2, 1999

[54] EMULSIFIER AND STRUCTURAL ANALYZER

[76] Inventor: Horace Wayne Duke, 2860 Hwy. 49, Pleasant View, Tenn. 37146

[21] Appl. No.: 895,317

[22] Filed: Jul. 16, 1997

[51] Int. Cl.$^6$ ............................. G01N 11/14; B01F 15/00
[52] U.S. Cl. ....................... 73/54.28; 73/54.31; 73/61.43; 422/68.1; 366/325.94
[58] Field of Search ................ 73/54.28, 54.31, 73/61.41, 61.43, 61.44, 866; 422/68.1, 73; 366/325.94

[56] References Cited

U.S. PATENT DOCUMENTS

| | | | |
|---|---|---|---|
| 2,074,174 | 3/1937 | Goodier | 265/11 |
| 2,305,531 | 12/1942 | Hurndall | 265/11 |
| 2,598,178 | 5/1952 | Källe | 73/357 |
| 3,053,078 | 9/1962 | Jewett | 73/54 |
| 3,111,838 | 11/1963 | Bucalo | 73/54 |
| 3,229,506 | 1/1966 | Bruss et al. | 73/59 |
| 4,334,424 | 6/1982 | Kepes | 73/59 |
| 4,403,867 | 9/1983 | Duke | 366/142 |
| 4,653,313 | 3/1987 | Sabins et al. | 73/61.4 |
| 4,930,346 | 6/1990 | Paakkinen et al. | 73/59 |
| 5,142,900 | 9/1992 | Duke | 73/54.39 |
| 5,321,974 | 6/1994 | Hemmings et al. | 73/54.31 |
| 5,606,115 | 2/1997 | Kamrat | 73/54.28 |

*Primary Examiner*—Hezron Williams
*Assistant Examiner*—J. David Wiggins

[57] ABSTRACT

Methods and apparatus that simulate the environment and conditions to which printers ink is subjected by the rollers and roller nips of a printing process, as well as determine the rheological characteristics of such ink across a range of water concentrations is disclosed, thus permitting a printing press operator to be assured of consistent ink film splitting (in "wet on wet" printing process), good ink to paper adhesion, good lithographic stability of inks or varnishes and good adhesion of one ink color to another ink color (i.e.—elimination of color chasing). The prior art is now benefited by helping to ensure that these inks, shellacs and varnishes function properly by keeping the amount of water added to the material within an acceptable range, despite the now known changes to rheological characteristics of printers ink caused by continuous hammering or pounding while subjected to action of roller nips in a printing press. To simulate such roller nips and determine rheology at various water concentrations and at different degrees of pounding or hammering, the apparatus uses a mixing member with a plurality of blades, which blades conform to the inside surface of a mixing cup; and which apparatus measures the force coupled by the ink/) varnish/shellac between the mixing member, as rotated at a selected constant speed by a precise motor, and the mixing cup, as water is added at a selected rate while hammering or pounding occurs, and/ or temperature changes of the ink/varnish/shellac occur.

18 Claims, 5 Drawing Sheets

EMULSIFIER AND STRUCTURAL ANALYZER

BACKGROUND OF THE INVENTION

The present invention relates generally to apparatus and methods for testing selected characteristics of viscoelastic fluids such as lithographic printer's ink and varnish. More particularly the invention relates to such methods and apparatus that measures the force coupled by an ink or fluid between two members that create a "nip" as they move relative to each other. More specifically, the apparatus of the present invention simulates the nip created by two rollers in a printing press. The apparatus is capable of making such measurements at various levels of water concentration and various relative speeds.

In the lithographic printing industry, it is important to understand that one does not print with "ink" but instead prints with an "ink-water emulsion". This "ink-water emulsion" is formed on the lithographic printing press when the lithographic printing ink and fountain solution (water with various additives) go through numerous roller nips on a printing unit(s) on a lithographic printing press. Inks in the lithographic printing industry are either considered "lithographically stable" or "lithographically unstable". A "lithographically stable" ink or varnish is an ink or varnish which exhibits little or no change in its high shear rheology (structure) as a result of variations in the amount of water emulsified into the ink or varnish as it passes through the numerous roller nips on a lithographic printing press. A "lithographically unstable" ink or varnish is an ink or varnish which exhibits significant changes in its high shear rheology as a direct result of variations in the amount of water emulsified into the ink or varnish as it passes through the numerous roller nips on a lithographic printing press. In the past it was generally believed in the lithographic printing industry that to print properly an ink or varnish must absorb a particular percentage of water (fountain solution). However, it is now understood that it is more important to know how ink's or varnish's high shear rheology changes as a result of the water (fountain solution) emulsification rather than simply how much water or fountain solution the ink will absorb. To determine the rheological values of a printing ink, most quality assurance labs use an inkometer to measure tack and misting, a "flow plate" to measure ink fountain flow behavior, a viscometer such as a "drop rod" viscometer or preferably the Duke Custom Systems, Inc. D-2000 viscometer to measure viscosity and stress at rates of shear from 2.5 sec-1 to over 7,500 sec-1, a flow plate to measure ink fountain flow behavior, and a Duke D-10 ink water emulsification tester to measure the water pick-up of inks.

The Duke D-2000 discussed in U.S. Pat. No. 5,142,900 issued to the present inventor describes a substantially automated viscometer. The D-2000 includes a series of high-shear rod, and collar viscometer elements that are designed to eliminate the problems associated with drop rod viscometers, and to provide accurate and reproducible rheological test data on highly structured viscoelastic printing inks, varnishes, resin solutions and flushes at higher and lower shear rates than possible with a drop rod viscometer.

The D-10 tester described in the U.S. Pat. No. 4,403,867 patent by Horace Duke was designed to provide empirical data for lab testing purposes. Some of the additives used to adjust ink or varnish based on the test data obtained from the D-10 have a detrimental effect on actual press performance. The D-10 was not designed to predict the stability of an ink\water emulsion at press speeds. None the less, it is not uncommon for an ink to be within specifications for various laboratory tests and still exhibit undesirable, unstable behavior on the printing press. When a printer or ink manufacture's lab is unable to detect this instability before the ink or varnish is used on a press, longer startup time, increased waste, reduced press speeds, and higher color variations are the result. These problems, of course, have a detrimental effect on a printer's efficiency and profitability.

The present invention, however, improves over the D-10 tester in that it allows a lab technician to quickly and easily make an ink/water emulsion that exhibits the characteristics of an emulsion formed on a high-speed press. It makes an emulsion of ink and water or fountain solution at velocities that range from as low as 100 LFM (linear feet per minute) to more than 3,000 LFM by emulating the different energy levels an ink experiences on the roller train(s) of lithographic printing press(es) passing through the roller nip. Press correlation tests have shown that this energy-input simulation is very important in generating emulsions with characteristics that mirror those found on high performance presses.

SUMMARY OF THE INVENTION

It is an object of the present invention to provide apparatus and methods for testing the structural integrity of viscoelastic fluids such as lithographic printers ink or varnish at various concentrations of water or fountain solution for which the apparatus can be pre-programmed, which requires little or no monitoring, and which closely simulates the compression and relaxation ("hammering or pounding") such inks or varnishes experience passing through the roller train nip(s) of a lithographic printing press at today's faster printing speeds.

It is a further object of the invention to provide apparatus and methods for testing the structural integrity of such fluids at selected temperatures and velocities.

The testing apparatus for testing such structural integrity comprises a rigid thermally conductive container or cup for holding the fluid to be tested which is rigidly supported by a support structure. The cup defines a bottom inside surface of a selected shape. Also included is a mixing member having a plurality of blades that is rotated by a drive means around a selected axis at a selected speed. The mixing member is suitable for being introduced into the rigid thermally conductive container to a selected position such that the rotating member is rigidly maintained and spaced at a selected distance from the bottom surface of the container as it rotates around the selected axis. Selected blades of the plurality of blades of the mixing member define an envelope which at least partially conforms to the bottom inside surface of the container such that a nip of a known spacing is defined between the bottom surface of the container and the envelope defined by the rotating mixing member. A sensing means measures the force coupled between the rotating mixing member and the container by the material under test. This measured force is directly related to the structural integrity and stability of the "ink-water" (fountain solution) emulsion.

The preferred embodiment further includes a means for accurately measuring the temperature of the material under test during the entire testing process, as well as a computer and related software to calculate the desired rheological characteristics from the data obtained from a given test sequence.

BRIEF DESCRIPTION OF THE DRAWINGS

The above mentioned features of the present invention will be more clearly understood from consideration of the following description in connection with the accompanying drawings in which.

AN EMBODIMENT FOR CARRYING OUT THE INVENTION

It is not uncommon for a lithographic printing press operator to ""chase"" colors while a job is printing. Although the quality and consistency of lithographic printing inks have improved greatly over the past decade, it is still all too common to see this phenomenon occur. The lithographic printing press brings ink and fountain solutions together at high velocity. This mixture of ink and fountain solution is subjected to high pressure "pounding" or "hammering" as it moves through the various roller nips which has the effect of squeezing the fountain solution into the ink. However, when more than one color of ink is used, a press may print an area 100% coverage on one side of the sheet or web of paper with 100% ink or varnish coverage (The term web is used to describe the single layer of paper from a roll of paper going through the high speed press.), while at the same time a small spot area of the same ink or varnish is printed on the other side of the sheet or web. The ink or varnish on the high coverage side is rapidly being consumed as it is applied to the web of paper moving through the printing press and consequently is only subjected to a small number of passes through the roller nips with the fountain solution. These few exposures to the roller nip emulsify only a small amount of solution into the ink.

On the other side of the sheet or web, however, the ink/varnish and fountain solution make many more passes through the roller nip before the ink is actually printed onto the web of paper moving through the printing press. This results in a higher percentage of emulsification because the ink/varnish and fountain solution are being re-exposed to the rapid compression, short dwell at high pressure, rapid decompression and longer dwell at low/no pressure during each revolution of each roller or each pass through roller the roller nip.

If the ink/varnish structure changes greatly with different percentages of fountain solution emulsification, the ink will appear to have a different tack or tracktrap across the sheet or web. Although, some inks undergo virtually no structural changes from the emulsification, others may have major changes in structure as the percentage of emulsified water or fountain solution increases.

As a result of experience with various types of presses and printing everything from high quality magazines to newspapers, the inventor has discovered that the desirable window of emulsion stability appears to be from a low of about 20% to a high of about 80% emulsification with a fountain solution. If the high-shear structure of an ink/fountain emulsion does not change substantially as the percentage of the fountain solution varies from 20–80 percent, the ink/varnish appears to be forgiving of press and job conditions and the skill of the press operator. However, the more the structural changes, the more sensitive the ink/varnish becomes to press conditions, job specifics, and the skill of the press operator.

Figure 1:
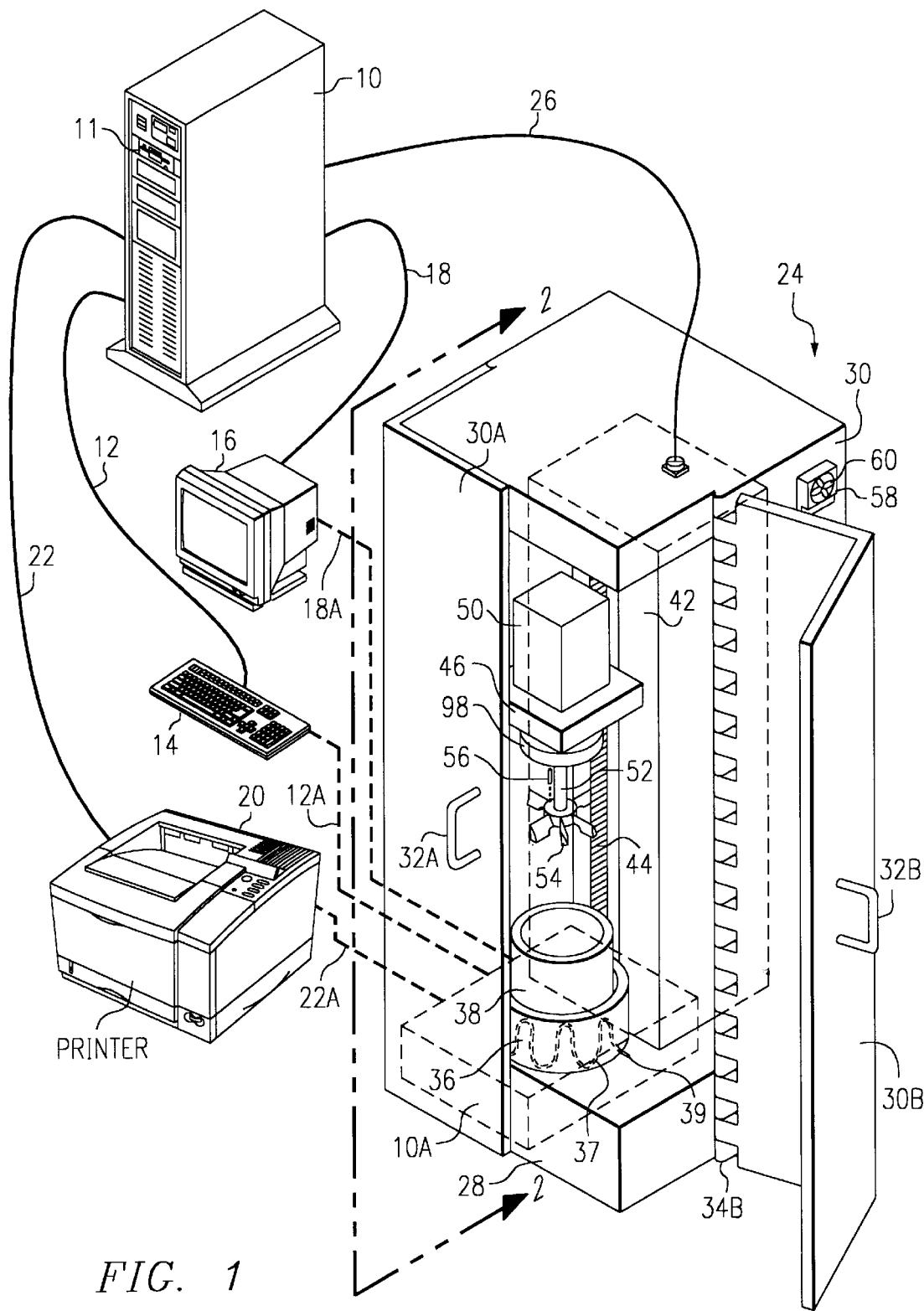
FIG. 1 is a perspective view of a preferred embodiment of the apparatus of the present invention.
Figure 2:
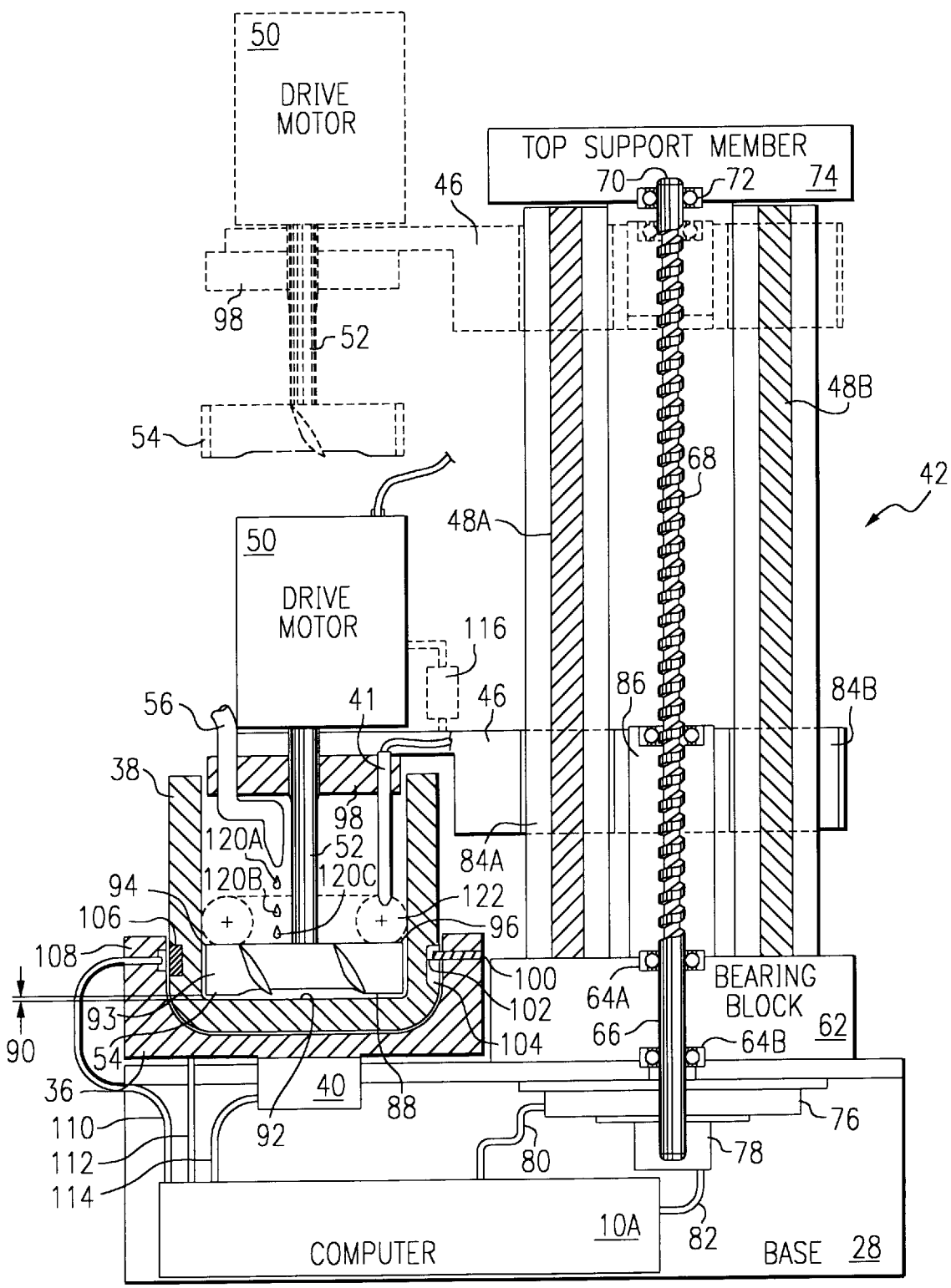
FIG. 2 is a cross-sectional view of the testing machinery portion of the apparatus of this invention taken along lines 2—2 of FIG. 1.

Referring now to the Figures, there is shown an embodiment of the present invention. As seen in FIGS. 1 & 2, the apparatus according to one embodiment includes a computer 10, such as any one of a number of available Personal Computers. In the embodiment shown the computer may be a "486" or more advanced type of computer having a floppy disk drive. Also connected to the computer 10 by cable 12 is a standard computer keyboard 14, a monitor 16 connected by a cable 18, printer 20 connected by cable 22, and the ink/varnish testing mechanism 24 connected to computer 10 by a cable or cables 26. Although for convenience, the computer 10, the keyboard 14, the monitor 16 and the printer 20 may be modified or otherwise combined, commercially available products are quite satisfactory. However, one particularly effective alternate embodiment is to incorporate the computer 10A into the base of the ink/varnish testing apparatus 24. This embodiment is represented in FIG. 1 by the cables 12A, 18A, and 22A shown in dotted lines that run from the keyboard 14, the monitor 16 and the printer 20 respectively to the computer 10A contained in the base 28 of testing mechanism 24. As shown, testing mechanism 24 includes base 28 surrounded by transparent enclosure 30. Enclosure 30 includes a pair of doors 30A & 30B with handles 32A & 32B (handle 32B not shown) and is supported by hinges 34A & 34B. Hinge 34A supports door 30A, but is not visible. Within enclosure 30 and mounted to base 28 is a support cradle 36 for releasably holding mixing container or cup 38. Since the stirring or mixing of viscoelastic fluids such as printing ink/varnish and the like generates a substantial amount of heat, support cradle 36 preferably includes a cooling jacket indicated symbolically by tubing 37 and a cooling fluid connection port 39.

Any suitable cooling fluid such as water, oil, freon or the like may be circulated through the cooling jacket. A temperature probe 41 extends down the sidewall of container 38 into a toroid of a mixture of water (fountain solution) and printing ink or varnish. The output of the temperature probe provides data as to the temperature of the water and ink/varnish mixture during testing and may also be used to control the temperature of the cooling fluid flowing through tubing 37 in the cooling jacket.

Although not shown in FIG. 1, and as will be discussed later with respect to FIG. 2, according to one embodiment, a sensor 40 may be mounted between support cradle 36 and base 28 to measure rotational torque applied to cup 38. Fixedly mounted to base 28 is carriage support structure 42 having a vertical pathway 44. A carriage support block 46 is mounted to carriage support structure 42 by means of a pair of slide rails 48A & 48B so that a drive mechanism can move carriage support block 46 up and down with respect to container or cup 38. Mounted to support block 46 is a powerful precision drive motor 50 that rotates shaft 52 and mixing member or blades 54 at a selected constant speed. Also extending from support block 46 is a water or liquid tube 56 which provides water, fountain solution or other selected liquid, at a known rate, to the top side of mixing member 54 where it is then disbursed as microdroplets into the fluid under test by the centrifugal force of mixing member 54.

It will be appreciated that during the formulation of certain fluids such as but not limited to Liquid and Paste types of printing inks and coatings, due to the interrelationship existing between temperature and rheological characteristics of fluids, it is of particular benefit to test such Theological characteristics at the same temperature that the fluid will experience during actual use. Therefore, particularly with respect to printing inks there is a need to measure the Theological characteristics across a range of temperatures which covers the different temperatures the fluid will encounter when used by different methods of printing. Temperatures at which printing inks typically may encounter on the printing press range from a low of approximately 20 degrees Centigrade to a high of approximately 40 degrees Centigrade. As will be described below, in addition to the cooling provided by a cooling fluid flowing through tubing 37, one embodiment uses an electronic heat pump capable of raising and/or lowering the temperature within the test enclosure from approximately 20 degrees Centigrade to approximately 50 degrees Centigrade.

More specifically, as discussed above, the apparatus may include a cooling jacket or tubing 37 for carrying a cooling fluid such as water, oil, freon or the like. Alternatively, or in addition to the cooling jacket, according to one embodiment, the invention includes a transparent enclosure 30 that provides safety as well as a controlled, stable-operating environment, isolated from ambient room environmental conditions, for the testing mechanism 24 of the apparatus. An electronic heatpump system 58 utilizing thermoelectric (Pettier) solid state heat pumps, efficient heat exchangers, high volume air movement devices (fan 60) and the necessary support electronics is incorporated for precisely controlling and maintaining a desired temperature within the enclosure. Although it is known that rheological characteristics are temperature sensitive, it is less well known that certain non-Newtonian fluids such as printing ink(s) may exhibit changes of rheological characteristics in excess of twenty percent per degree centigrade. Due to this high sensitivity, minute changes in temperature of fluids, such as printing inks, may cause significant rheological characteristic changes. Consequently, it will be understood that precise and accurate temperature measurement and control is critical if highly accurate measurements of rheological characteristics of fluids are to be obtained. Thus, temperature controlled enclosures, such as are commonly known and used in the industry, to maintain the internal temperatures of an enclosure within plus or minus 0.5 degree centigrade are inadequate when performing precision testing of rheological characteristics of fluids. Further, without a method to circulate and mix the air inside the enclosure, the air would stratify and the inside of the enclosure would not be at a uniform temperature.

Therefore, in order to maintain a temperature inside the enclosure 30 of one embodiment of the present invention within the desired range of plus or minus one-tenth (0.1) of a degree Centigrade, the temperature control apparatus must be capable of detecting changes as small as one one-hundredth (0.01) degree Centigrade and then accurately and quickly raise or lower the temperature of the air stream circulating through the heat-pump heatsink and enclosure. The temperature stabilized air stream may be distributed throughout enclosure 30 by baffles to assure uniform distribution. The air stream is typically recirculated approximately fifty times per minute.

Also mounted to and supported by base 28 is a carriage support structure 42. In the embodiment shown, the carriage support structure 42 includes a pair of elongated slide rails 48A and 48B mounted perpendicular to base 28 by way of bearing block 62 such that both rails 48A and 48B are orientated in a vertical position. Bearing block 62 is secured to base 28 and incorporates two sets of aligned bearings 64A and 64B for rotationally supporting the bottom portion 66 of an elongated precision "ball screw" 68 which is aligned parallel to elongated slide rails 48A and 48B. The top end 70 of ball screw 68 is rotationally supported by bearing 72 mounted in top support member 74. The bottom end of ball screw 68 is connected to a rotational drive means such as motor 76. Motor 76 is preferable a motor that can supply a smooth non-cogging rotational drive power. In the illustrated embodiment, the rotational position of ball screw 68 is precisely controlled by motor 76 in cooperation with encoder 78, and computer 10(10A) through wires 80 and 82 respectively.

Carriage support block 46 includes two sets of double linear bearings, 84A and 84B which travel along elongated rails 48A and 48B. A zero backlash preloaded ball-nut 86 that travels along ball screw 68 when ball screw 68 is rotated, is secured to carriage support block 46. Thus, rotation of ball screw 68 by motor 76 results in precise vertical movement of carriage support block 46 along slide rails 48A and 48B.

Referring to FIG. 2, both the raised position and the lowered position (operating position) are shown. Because of the precise control of the vertical position provided by the motor 76, encoder 78 and computer 10 (10A) the carriage support block 46 can be lowered such that the bottom surface 88 of a portion of the plurality of blades on mixing member 54 is spaced a precise distance 90 from the inside bottom surface 92 of mixing cup or container 38. According to the illustrated embodiment, the distance is selected between $10/1000$ inch to $15/1000$ inch and is repeatable to 0.0001 inch. It should also be noticed that in one embodiment, the spacing between the side walls of container 38 and the ends of blades 54 is about one fourth inch and that this spacing is not critical to benefit from the advantages of the invention. However, referring to FIG. 5, additional benefits may be achieved if the ends of blades 54 have a close tolerance with respect to the cup or container by conforming the ends of the blades with the inside walls of cup or container 38 as indicated by the extension 93 of the ends of blades 54 as shown in dashed lines. If such close tolerances are to be achieved, the mixing cup or container 38 and the carriage support block 46 (and consequently the mixing member or blades 54) are also rigidly maintained in the horizontal position such that a much smaller spacing 94 is maintained between the mixing member envelope produced when the blades rotate and the inside side surfaces 96 of mixing cup or container 38. Although, unlike spacing 90 the spacing 94 may vary significantly. However, it is still of utmost importance that as mixing member or blades 54 rotate at a high speed they must not come into contact with the inside side surfaces 96. In a typical testing operation, motor 50 rotates mixing member 54 at a speed which simulates the velocity at which the surface of the sheet or web of paper moves through the printing press the printing press roller nips as the web of paper travels through the press. To accurately simulate the energy input levels an ink/varnish experiences on a printing press, mixing member 54 may well rotate at a speed of over 5,000 RPM. Several high torque, constant high-speed motors may be suitable, however, a DC brushless servomotor made by Glentek, Inc. has been especially effective.

Referring to FIG. 2, it should also be noted that when carriage support block 46 is in the lowered position, a cover block 98 may be provided to affect a fit which substantially seals mixing container 38. Cover block 98 provides two functions. First, it helps assure that rotating mixing member 54 will not contact the inside side surfaces 96 of the mixing cup 38. Second, it substantially seals container 38 such that water vapor (or other liquid vapor) cannot escape from container 38. This is important in helping to maintain a constant enclosure 30 temperature and a constant humidity level inside the container 38.

Also as shown, in FIG. 2, a locking pin 100 located in support cradle 36 is received by locking notch 102 in mixing cup or container 38 via groove 104 to lock the mixing cup in a rigid position during operation. According to one embodiment, a small permanent magnet 106 may be embedded in the mixing cup or container 38. When permanent magnet 106 is positioned adjacent a reed switch 108 in support cradle 36, the reed switch will be activated so as to provide a signal to computer 10 (10A) by wire 110 to indicate that the mixing cup 38 is properly locked in position in support cradle 36. In an alternative embodiment, one or more additional reed switches (not shown) may be mounted at different locations in support cradle 36, as is indicated by wire 112. Although a total of two or more reed switches may be provided, typically each individual mixing cup or container 38 will have only one permanent magnet 106, and in different mixing cups the permanent magnet 106 will be mounted in different locations. Therefore, depending on which reed switch is activated, a particular cup can be identified as being present in the support cradle 36 as well as indicating that the cup is locked in position. Of course, for more complicated cup-identifying arrangements, each cup could include two or more permanent magnets embedded at selected locations. Other methods of identifying which bowl 38 is inserted into cradle 36 could be utilized.

The force that is imparted to the mixing cup 38 by the material under test as member 54 rotates is directly proportional to the molecular friction of the material under test, the relative velocity of the mixing member 54 to the mixing cup, inversely proportional to the clearance or space 90, and the temperature of the fluid under test. In one embodiment, to measure this force, load cell or strain gauge 40 is connected between the support cradle 36 and base 28 for measuring the rotational force or torque coupled between the mixing member 54 and mixing cup or container 38 by the printers ink or other fluid under test. The output of load cell 40 is provided via wires 114 to computer 10 (10A) where the necessary signal conditioning and conversion from an analog signal to a digital signal is accomplished for subsequent calculations by the computer 10 (10A). In a preferred embodiment, an ultra precision strain gauge type load cell having a capacity of between about 0.00 grams and about ten (10) kilograms has been found to be particularly suitable for testing printing inks. According to an alternate embodiment, in place of load cell 40, load cell 116 may be connected between carriage support block 46 and drive motor 50 as shown in dashed lines. Load cell 116 also measures the force coupled between rotating member 54 and cup 38 just as did load cell 40. Still in another alternate embodiment, both load cells 40 and 116 could be connected as shown and then the outputs of both load cells combined and/or compared to increase accuracy. It will also be apparent that the coupled force can be determined without the use of a load cell at all. If motor 50 receives its power from a stable power supply and has a constant current/torque ratio, and the variations in the drive current to motor 50 are measured, the variations in the drive current will be proportional to the torque or force coupled by the liquid under test between the mixing member 54 and the mixing cup 38.

Figure 3:
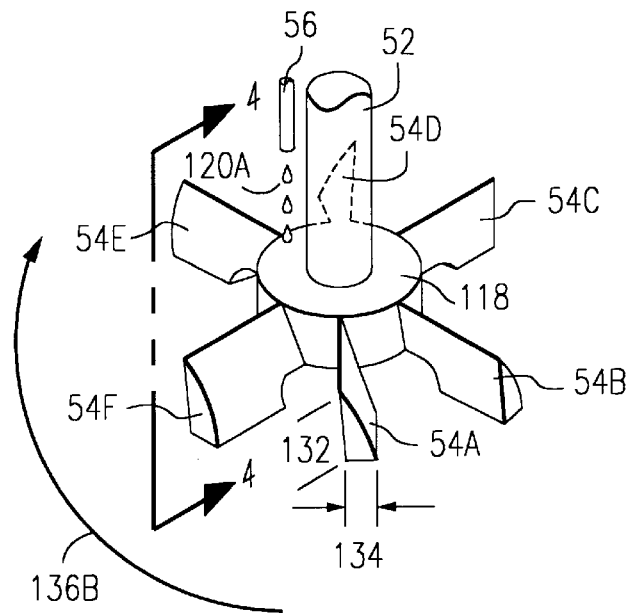
FIG. 3 is a perspective view of the mixing member having a plurality of blades according to one preferred embodiment of the invention.
Figure 4:
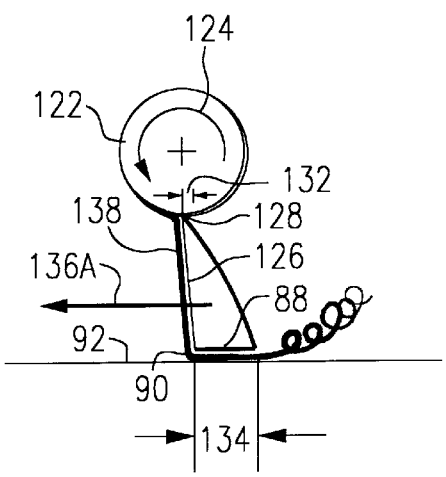
FIG. 4 is an end view of a single blade of the embodiment of FIG. 4 showing the toroid of a fluid under test produced by the rotating mixing member. Also shown is the flow direction of the fluid through the nip between the bottom of the blade and the bottom inside surface of the mixing cup or container.
Figure 5:
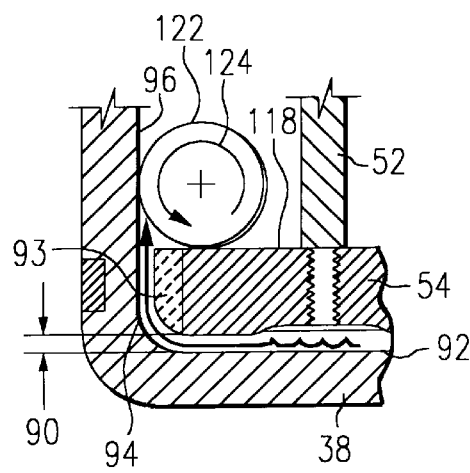
FIG. 5 is a cross-sectional side view, according to one embodiment of the present invention, showing the nip formed by the bottom of the cup or container and the mixing member. The flow direction of the fluid under test in forming the toroid at the top of the rotating mixing member is also shown.

Referring now to FIGS. 3, 4 and 5 there is shown details of an embodiment of a mixing member having six blades. However, it should be understood that although the number of blades is not critical, six blades provides excellent balance of the forces on the rotating shaft without excess wear of the blades while still effecting an excellent simulation of the "nip" between two rollers of a printing press. As shown in FIG. 3, shaft 52 supports the mixing member 54 with the six blades 54A, 54B, 54C, 54D, 54E and 54F. A hub section 118 is provided which has a flat surface where water or another diluting liquid may be directed at a known flow rate. This is shown by drops 120A, 120B and 120C from tube 56 in FIGS. 2 and 3. The six blades, such as blade 54A extend radially from hub 118 and have a cross section taken along lines 4—4 as shown in FIG. 4 and will be discussed later. The high speed rotation of mixing member 54 and the resulting centrifugal forces on the drops of water as they hit the top surfaces of hub 118 of the mixing member breaks the drops of water into "microdroplets" which are disbursed into the emulsion with uniformity. This uniformity aids in the precision of the invention. FIG. 5 is an enlarged cross section of a portion of the mixing cup 38 and the mixing member 54 of FIG. 1 showing the toroid of fluid 122 produced by centrifugal force and the rotating mixing member 54. The direction of rotation of the toroid of fluid is indicated by curved arrow 124. FIG. 5 also shows how the liquid under test collects at the bottom of the mixing cup and is then forced up the sides of cup 38 by the centrifugal force of the liquid produced by rotating blades 54A–54F.

It is known that the "hammering" or "pounding" of printers ink/varnish passing through the nip of two rollers on a printing press affects certain characteristics of the ink such as adhesion to paper, water absorption, structural integrity, etc. Further the inventor has discovered that the torque or force coupled between the mixing member and the container of the inventive apparatus is proportional to certain of the fluid characteristics and that the "hammering" or "pounding" that a fluid experiences as it passes through the nip of two rollers in a printing press can be simulated by the proper design of the mixing member and container.

More specifically as shown in FIGS. 3 and 4, each blade has an oblique trapezoidal cross-section such that the front face 126 of each blade extends from a cutting or leading edge 128 to a trailing front edge 130. Also as shown in the embodiment of FIGS. 3 and 4 the top width dimension 132 of a blade is smaller than the bottom width dimension 134. Therefore, in operation as the blades rotate as indicated by arrows 136A and 136B the shape of the mixing member 54 and the container 38 work together to produce the toroid of fluid 120 which rides the outside top surface of the mixing member 54. However, gravity of course, also acts on the toroid of fluid and tries to cause the fluid to flow down over the blades. Therefore, the cutting or leading edge 128 cuts a small layer of the fluid 138 from the bottom of the fluid toroid 122 and accelerates the slice of fluid down the front surface 126 of the blade and into the gap or nip 90 where the ink experiences the hammering or pounding similar to that experienced by ink passing through the roller nip of a printing press. To achieve this, the rotational speed of the mixing member 54 or impeller is set so that the velocity of the ink is the same the as it would be when the paper sheet or web moves through the printing press. This pounding effect is due to the ink acceleration past the face 126 of the rotating blade then passing through the narrow clearance 90 between and the rigid bottom surface 88 of the blades and the bottom inside surface 92 of the cup or container 38. It should also be noted that mixing the pounding and hammering of the ink created by the rotating blades on mixing member 54, can result in significant wear of the blades. To, help prevent such wear, the material of the blades is preferably surfaced hardened in excess of Rockwell C-60. For example, in a preferred embodiment, which uses aluminum for the mixing member, the surface of the blades is provided with a very hard anodizing. It should also be noted that although the described embodiment shows each blade to be similar and contribute to producing the "hammering" or "pounding" of the Ink or varnish, it is possible to provide a mixing member where selected ones of the blades are working blades and do the hammering while other blades have a different shape and a different function.

The apparatus of the present invention is designed to operate in at least two modes. In the first mode, the apparatus starts a test and measures structural changes as an ink or varnish fountain solution or water is emulsified by fountain solution or water at press velocities. The fountain solution or water is added to the ink or varnish until the emulsion formed by the ink or varnish and water or fountain solution becomes unstable as the emulsion passes through the narrow clearance 90 between the bottom of each blade 88 and the inside surface of the cup 96. This emulates use of the emulsion in a high-speed press where most ink/fountain solution emulsions become increasingly unstable as the speed at which the web of paper travels through the press rises. The computer printer included in the test apparatus of the present invention prints a graph showing the changes in ink structure as the fountain solution is added as well as summarizing structural changes that occur along the actual test parameters. By comparing the graphs it is possible to identify trapping problems and determine whether they are the result of incompatibilities between the printing ink and the fountain solution. It is also possible, to evaluate the effects caused by changing the chemical composition of either the ink or fountain solution. Increased stability or decreased stability of the resulting emulsions formed can be easily measured and compared.

In the second mode, the apparatus is used to generate emulsions at specific percentages of emulsified fountain solution or water. These emulsions can then be tested on a viscometer such as the D-2000 described in U.S. Pat. No. 5,142,900 discussed above, and incorporated herein by reference. By obtaining a complete set of flow curves from 2.5 sec-1 to 10,000 sec-1 the structural rheological effects that occur at known rates of shear as a result of varying the level of the emulsified fountain solution can be observed. This type of testing can help identify lithographically stable and unstable inks at known higher shear rates. It also enables the operator to check the compatibility of different ink\fountain solution emulsions. The operator can then vary components in the ink or fountain solution and document the effect of these changes on the emulsion. By combining the emulsion test data obtained from the apparatus of the present invention with reliable data obtained from viscosity testing (such as is available from the Duke-2000 viscosity tester), the stability of lithographic printing inks on high speed presses can be reliably predicted. The test data shows whether an "ink set" (a selection of two or more colors of ink) will have color chasing (or trapping) problems before the ink set is ever placed in use on the press.

Operation of the apparatus of this invention that has been calibrated typically proceeds as follows in the first mode or testing mode. A known amount (such as 100 grams) of the material to be tested (such as printers ink, varnish, shellac, etc.) is placed in the cup or container 38. Cup 38 is then secured into the support cradle 36. The enclosure doors 30A and 30B are then closed. Carriage support block 46 (and consequently motor 50 and mixing member 54) is then lowered about halfway, but not so low that mixing member 54 contacts the material being tested. Multi-bladed mixing member 54 is then brought up to the desired test speed and various diagnostic and safety checks can be ran. For example, a torque reading from load cell 40 can then be taken, which in normal operation represents the force coupled between mixing member 54 and container or cup 38 by the material being tested. Of course, since mixing member 54 is not in contact with the test material in cup 38 there should be no coupling force. Thus any reading of torque ("TARE" value) is used to zero out or offset any torque measured in the system which is not actually generated from the material under test. This is especially significant when the motor current is measured in order to determine torque measurements. Tare is a term used to indicate the system load, which is not caused by the material under test. Carriage support block 46 is then further lowered, which, of course, lowers mixing member 54 into the test material. Carriage support block 46 is lowered until the bottom portion of mixing member 54 is at the test position or at a selected spacing of between $10/1000$ inch to $15/1000$ inch from the bottom inside surface of the mixing cup or container 38. Before the mixing member 54 contacts or moves into the test material, which is typically a heavy thick paste, it may be desirable to slow the rotational speed of mixing member 54, and then once the mixing member 54 is fully in the test material bring the rotational speed back up to test velocity, and maintain the speed until the material and apparatus has achieved stability or equilibrium.

That is, the torque on support cradle 36 as measured by load cell 40 and displayed on monitor 16 or printed on printer 20 is constant for at least 30 seconds. The time to reach such a stable condition should be in the range of between one minute and 10 minutes, and is typically about three minutes.

The mixing member is then raised so that it is out of the material and another TARE reading is taken to make sure that the torque characteristics of motor 50 have not changed. The mixing member 54 is then again lowered into the test material and ran for a short period of time to assure that the test material is still stable or at equilibrium. It will be appreciated that at this point no water or fountain solution (water with chemicals added) has been added to the test material. Water or a fountain solution is then dispensed at a known rate by being directed to the top surface of hub 118 of mixing member 54 and disbursed and mixed into the test material as the torque readings are recorded and/or displayed on monitor 16 and/or printed out at printer 20. With the aid of computer 10 (10A), the torque readings are taken at a rate of over 10,000 per second. The readings which occur while the first one- percent of water or fountain solution is added should be ignored since the changes during this early stage of the test are typically radical and unpredictable.

The responses or readings are usually similar for lithographically stable inks or varnishes in the same family and typically show an initial drop in the coupled force or torque when the fountain solution or water is added and then the torque will climb until it stabilizes at about 15–20 percent emulsion. The mixture or emulsion of a lithographically stable material will then typically stay stable until a level of between 50–80 percent emulsion is reached at which time it rapidly becomes unstable. Instability at the high levels of emulsion percentages occurs when the water and ink under go a "phase reversal". That is, in an emulsion, initially stable and up to the instability level, molecules of water are intimately bound to molecules of ink. Then, at the point of "phase reversal" the "intimate" molecular bond of ink and water is broken and "free" droplets of water are formed in the emulsion. Since the molecular friction of water is not as high as the ink, the free water droplets in high compression gap 90 mixture do not resist the rotation of the mixing member nearly as forcibly as the "in phase" ink/water emulsion mixture and the coupled force or torque reading by load cell 40 will be noticeably less.

Figure 6:
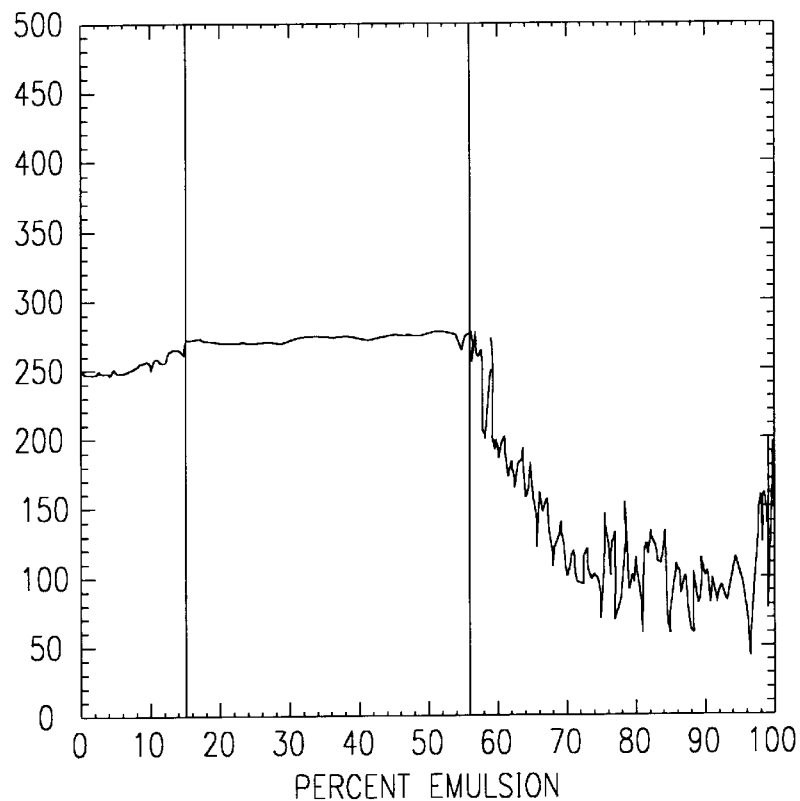
FIGS. 6 through 9 are actual graphs produced by one embodiment of the apparatus of the present invention showing results of the measured force coupled between the liquid container and the mixing member by various inks.

Referring now to FIGS. 6–9 there are shown actual graphs produced by the apparatus of this invention showing the lithographic structure as a function of the percentage of emulsification. The graphs show various results of a single color ink, and also the combined graph of a set of inks of four colors. FIG. 6 shows a rather typical graph of a satisfactory ink and water mixture. The graph represents the lithographic structure of the emulsion as calculated from the torque readings coupled between the mixing member 54 and cup or container 38 as determined by load cell when plotted against the percentage of emulsification. The rotational speed of the mixing member was chosen to emulate a paper web speed of 1000 LFM (linear feet per minute). The material was a red printer's ink and was maintained at a temperature of about 43.5 degrees centigrade. The graph shows that the material became stable at about 15% emulsification and remained stable until an emulsification of about 56% was reached. At that point the graph clearly indicates that the emulsification became unstable. Table 1 illustrates the conditions of the test.

TABLE 1

| Emulsion Time | 1252 seconds |
| --- | --- |
| Avg. Temperature | 43.5 degrees C. |
| Emulsion Capacity | 56% |
| Result | 10% structural deviation between 15% & 56% Emulsion at 1000 LFM |

Figure 7:
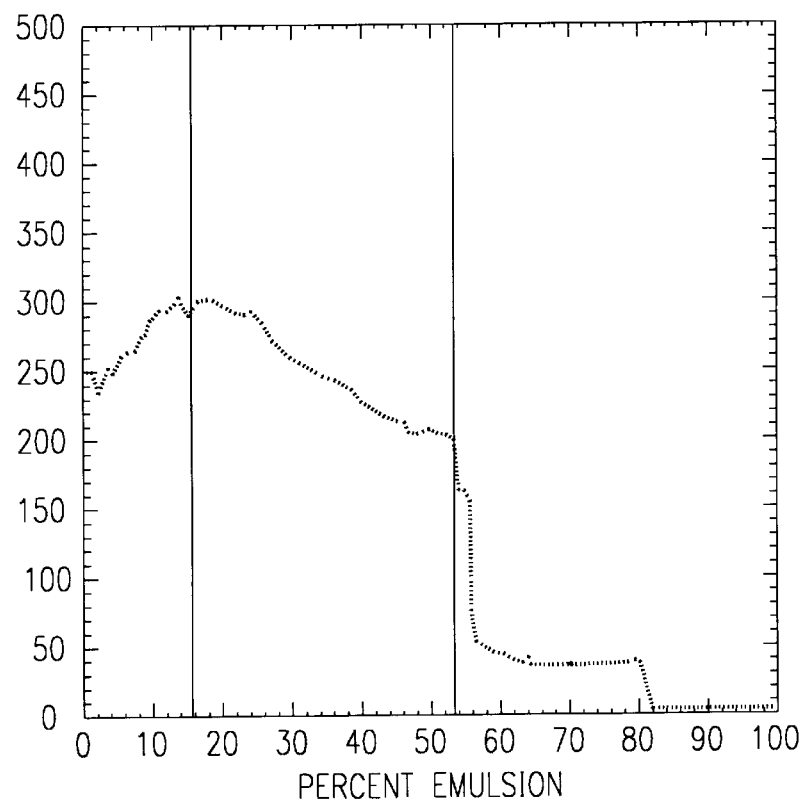

FIG. 7, illustrates a graph where there was a compatibility problem between the ink and the fountain solution. Table 2 shows the conditions of the test. Note that the material is not very stable even between the 15% and 55% emulsion levels, goes through a major structure change between about the 53% and 57% emulsion level, and then becomes stable for a short range of between 57% and 80% emulsification. The results of this test would indicate that major problems could be expected if a combination of this ink and fountain solution were to be used on a printing press.

TABLE 2

| Emulsion Time | 628 seconds |
| --- | --- |
| Avg. Temperature | 39.1 degrees C. |

TABLE 2-continued

| Emulsion Capacity | 53% |
| --- | --- |
| Results | 10% structural deviation between 15% & 53% Emulsification at 1000 LFM |

Figure 8:
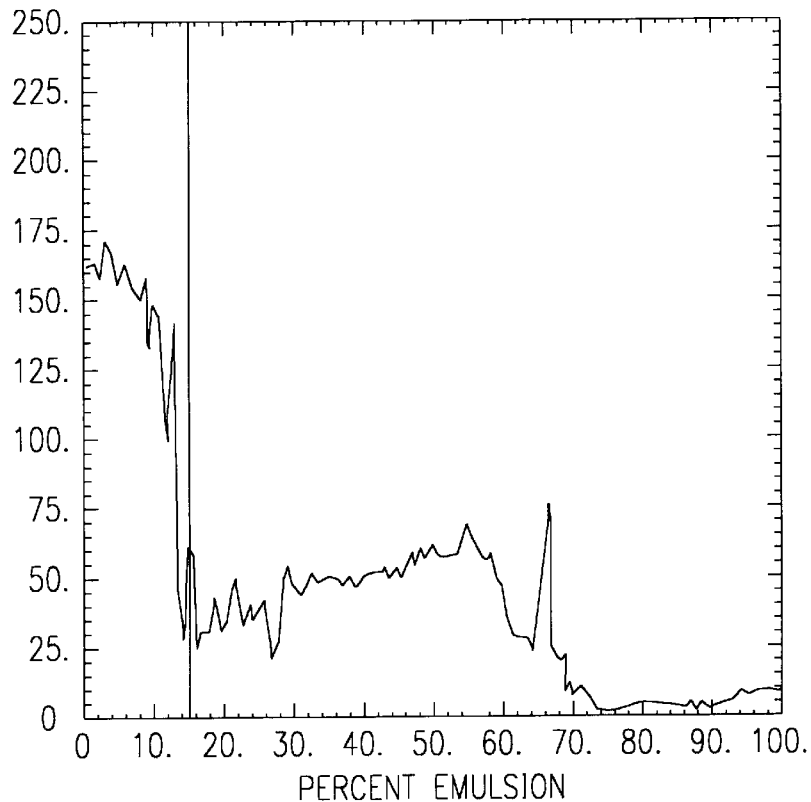

FIG. 8 and Table 3 illustrates another clearly unstable and unsuitable batch of ink that should not be used.

TABLE 3

| Emulsion Time | 628 seconds |
| --- | --- |
| Avg. Temperature | 46.6 degrees C. |
| Emulsion Capacity | 0% |
| Results | 3276.8 structural deviation between 15% & 0% Emulsification at 3000 LFM |

Figure 9:
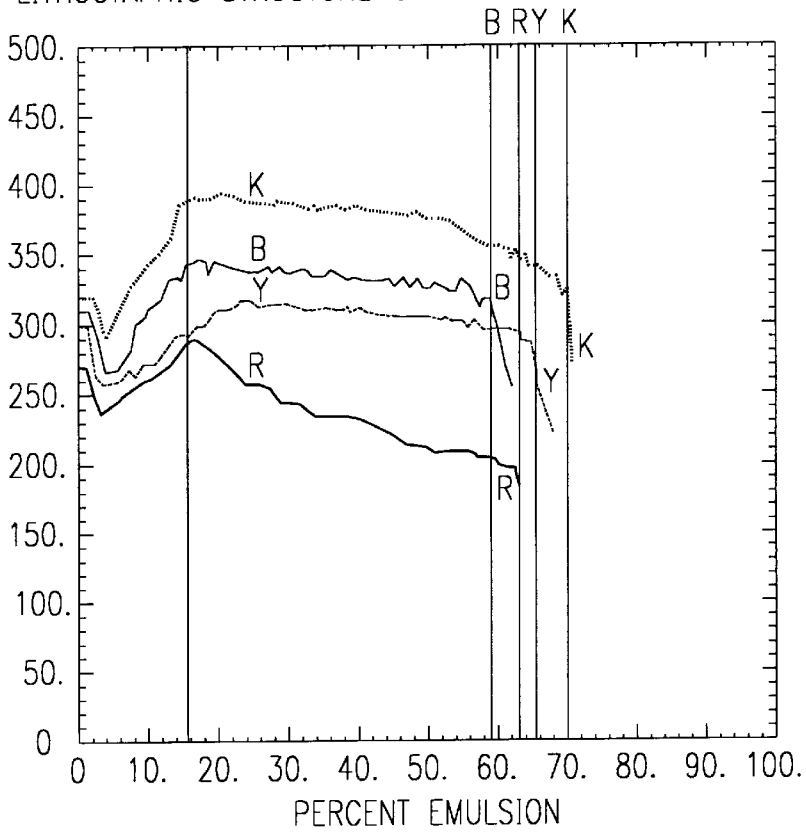

FIG. 9 illustrates a graph where four inks having different colors (red, blue, yellow and black) were tested and plotted. Table 4 shows the conditions of the test. This graph shows a partially stable and satisfactory "set" of inks for a multi-colored printing job between about the 15% emulsification level to the 60% emulsification lever. It is important to understand that in a satisfactory "set" of inks the relative levels or positions of the lithographic structures of the four inks do not change. That is, the graph lines do not cross in the useable areas. If the graph lines do cross, a poor or completely unsatisfactory printing job can be expected. As can be noted in this graph line representing the Black ink labeled "K", is above, approximately parallel to and does not cross the line for the Blue ink labeled "B". The line representing the Blue ink, labeled "B", is above and does not cross the red or yellow ink line. The line representing the Yellow ink, labeled "Y" is below and approximately parallel to the Blue ink line. These three inks, Black, Blue and Yellow are relatively lithographically stable from 20% through 60–68%. The Red ink represented by the line labeled "R" continuously changes as the percent of water changes. The Red ink would be referred to as a "lithographically unstable" ink. This continuous change in structure which results from different percentages of Water or fountain solution emulsified into the ink causes printing problems on a multicolor printing press. The variations in Red ink film thickness which is applied to the surface of the paper as the paper moves through the printing press causes severe variations in the perceived color on the printed paper.

TABLE 4

| Emulsification Time | 392 seconds |
| --- | --- |
| Avg. Temperature | 34.3 degrees C. |
| Emulsion Capacity | 63% |
| Results | 42.2% structural deviation between 15% & 63% Emulsification at 500 LFM |

Therefore, it will be appreciated that there has been described to this point an apparatus and methods for simulating the emulsification characteristic changes of printing ink due to the hammering and pounding the emulsification of ink and fountain solution undergoes from the roller nips of a high-speed printing press. Further the present invention has been described with respect to specific embodiments, and it is not intended that such specific references be considered as limitations on the scope of this invention except insofar as set forth in the following claims.

I claim:

1. Apparatus for determining the structural integrity of a fluid comprising:

a support structure;

a rigid container for holding a fluid to be tested, said container having a bottom inside surface of a selected shape, said container further being rigidly supported in a selected position by said support structure;

a mixing member having a plurality of blades, said member suitable for being introduced into said container and suitable for rotation around a selected axis, at least a portion of said plurality of blades defining an envelope at least partially conforming to said inside bottom surface of said container, and said support structure supporting said mixing member at a selected position in said container such that the conforming portion of said plurality of blades is rigidly maintained at a selected spacing from said inside surface of said container to define a nip (or area of high compression) between said blades and said inside surface with the rotation of said mixing member in said container;

driving means for rotating said mixing member around said selected axis at a selected speed while said mixing member is maintained at said selected position in said container;

a source of fountain solution provided at a known rate to the top side of said mixing member such that the centrifugal force of said mixing member breaks up said fountain solution into smaller droplets; and sensing means for measuring the force coupled between said rotating mixing member and said container by a fluid under test.

2. The apparatus of claim 1 and further comprising a computer for controlling selected test parameters of said apparatus and for monitoring and recording the results.

3. The apparatus of claim 1 and further comprising means for maintaining said rigid container within a selected temperature range.

4. The apparatus of claim 1 wherein said rigid container is releasably secured to said support structure.

5. The apparatus of claim 1 wherein the ends of selected blades conform to the inside sidewalls of said rigid container.

6. The apparatus of claim 1 wherein said sensing means comprises a strain gauge connected between said support structure and said rigid container.

7. Apparatus for determining the structural integrity of a fluid comprising:

a support structure;

a rigid container for holding a fluid to be tested, said container having a bottom inside surface of a selected shape, said container further being rigidly supported in a selected position by said support structure;

a mixing member having a plurality of blades, said member suitable for being introduced into said container and suitable for rotation around a selected axis, at least a portion of said plurality of blades defining an envelope at least partially conforming to said inside bottom surface of said container, and said support structure supporting said mixing member at a selected position in said container such that the conforming portion of said plurality of blades is rigidly maintained at a selected spacing from said inside surface of said container to define a nip (or area of high compression) between said blades and said inside surface with the rotation of said mixing member in said container, wherein said mixing member comprises a shaft concentric with said axis of rotation and said plurality of blades attached to and extending from said shaft, selected blades of said plurality including a bottom surface conforming to said inside bottom surface of said container and providing compression of the fluid under test, said conforming bottom surface extending a selected distance between a front edge and a trailing edge and a top portion of said selected blades having a cutting edge, said conforming surface defining said envelope during rotation, said cutting edge providing the leading portion of said blade during rotation such that a front surface extends from said top cutting edge downward and opposite the direction of rotation to said front edge of said conforming surface;

driving means for rotating said mixing member around said selected axis at a selected speed while said mixing member is maintained at said selected position in said container; and sensing means for measuring the force coupled between said rotating mixing member and said container by a fluid under test.

8. The apparatus of claim 7 wherein each of said blades of said plurality compress the fluid under test.

9. The apparatus of claim 7 wherein the selected spacing between said conforming envelope and the inside bottom surface of said container is between $10/1000$ inch and $15/1000$ inch plus or minus $1/1000$ inch.

10. The apparatus of claim 7 wherein the blades are surfaced hardened.

11. The Apparatus of claim 7 and further comprising a source of water provided at a known rate to the top side of said mixing member such that the centrifugal force of said mixing member breaks up said water into smaller droplets.

12. The apparatus of claim 9 wherein said support structure locates and maintains said selected spacing between the conforming envelope of said mixing member and the inside surface of said container.

13. The apparatus of claim 7 wherein said selected blades of said plurality further includes a back or lagging surface extends from said top cutting edge downward and opposite the direction of rotation to said trailing edge of said conforming surface.

14. The apparatus of claim 7 and further comprising a computer for controlling selected test parameters of said apparatus and for monitoring and recording the results.

15. The apparatus of claim 7 and further comprising means for maintaining said rigid container within a selected temperature range.

16. The apparatus of claim 7 wherein said rigid container is releasably secured to said support structure.

17. The apparatus of claim 7 wherein the ends of selected blades conform to the inside sidewalls of said rigid container.

18. The apparatus of claim 7 wherein said sensing means comprises a strain gauge connected between said support structure and said rigid container.

* * * * *